United States Patent [19]

Powanda et al.

[11] Patent Number: 4,868,329

[45] Date of Patent: Sep. 19, 1989

[54] ACCELERATED PREPARATION OF CARBOXYLIC ACID ESTERS

[75] Inventors: Thomas M. Powanda, Middlesex; Robert H. Imes, Bridgewater; George L. Collins, Maplewood, all of N.J.

[73] Assignee: Hoechst Celanese Corp., Somerville, N.J.

[21] Appl. No.: 168,565

[22] Filed: Mar. 7, 1988

Related U.S. Application Data

[63] Continuation of Ser. No. 891,990, Aug. 1, 1986, abandoned.

[51] Int. Cl.$^4$ ............................................. C07C 69/52
[52] U.S. Cl. ................................... 560/205; 560/100; 560/103; 560/130; 260/410; 260/410.5; 260/410.0; 260/410.9 R; 260/410.9 N
[58] Field of Search ............... 560/205, 100, 103, 130; 260/410, 410.5, 410.6, 410.9 R, 410.9 N

[56] References Cited

U.S. PATENT DOCUMENTS

| | | | |
|---|---|---|---|
| 2,426,968 | 9/1947 | Grubb et al. | 560/263 |
| 2,628,178 | 2/1953 | Burnett et al. | 560/224 |
| 2,917,538 | 12/1969 | Carlyle | 560/205 |
| 2,947,779 | 8/1960 | Idol et al. | 560/205 |
| 3,354,199 | 11/1967 | Lachowicz et al. | 560/205 |
| 4,187,383 | 2/1980 | Cowherd, III et al. | 560/224 |
| 4,250,328 | 2/1981 | Fujita et al. | 560/205 |
| 4,280,009 | 7/1981 | Erpenbach et al. | 560/205 |

OTHER PUBLICATIONS

*Hackh's Chemical Dictionary*, 4th Ed. (1969) McGraw-Hill, Publ. p. 424.
Kirk-Othmer *Encyclopedia of Chemical Technology*, 2nd Ed. (1963) vol. 1, p. 856.

*Primary Examiner*—Paul J. Killos

[57] ABSTRACT

The instant invention involves a process for preparing carboxylic acid esters which comprises coreacting a carboxylic acid and an aliphatic mono or polyol by maintaining one of the reactants in a reactor at elevated temperatures and adding the other reactant to the reactor over a period of time. By employing this process esterification times are significantly reduced.

18 Claims, No Drawings

ACCELERATED PREPARATION OF CARBOXYLIC ACID ESTERS

This is a continuation of co-pending application Ser. No. 891,990 filed on 8/1/86 abandoned.

BACKGROUND OF INVENTION

1. Field of Invention

This invention relates to chemical reaction processes. More particularly, this invention relates to highly efficient processes for preparing carboxylic acid esters.

2. Prior Art

The preparation of carboxylic acid esters has been carried out employing a wide variety of chemical reaction processes. For example, carboxylic acid esters have been prepared by reacting corresponding carboxylic acids, acid anhydrides or acid chlorides with various hydroxyl containing materials.

One important category of esterification reactions involves the formation of acrylic or methacrylic acid esters of mono or polyhydric alcohols. U.S. Pat. No. 4,053,504 and U.S Pat. No. 4,059,721 are typical of the patents relating to processes for forming acrylate esters. Both of these patents involve processes wherein essentially "cold" reactants are mixed together in a reactor and heated to reaction temperature. As the reaction proceeds, the water of reaction is removed and the temperature continues to rise until the reaction is completed.

In general, uncatalyzed carboxylic acid-based esterification reactions are relatively slow, often requiring as long as 12 to 24 hours to complete.

Accordingly, it is an object of this invention to conduct an esterification process which reduces the time necessary to carry esterification reactions to completion.

It is another object of this invention to reduce the costs of conducting esterification reactions by reducing the amount of time necessary to carry out the reaction.

It is yet another object of this invention to permit the rapid preparation of carboxylic acid esters without the use of catalysts such that the resulting products can advantageously be used as lubricants and as dielectric fluids.

These and other objectives are obtained by carrying out the process of the instant invention.

SUMMARY OF INVENTION

Disclosed herein is a process for the expeditious preparation of carboxylic acid esters which involves the co-reaction of a carboxylic acid and an aliphatic mono or polyol by maintaining one of the reactants in the reactor at elevated temperatures and by adding the other reactant to the reactor over a period of time. Using this process it is possible to significantly improve the speed of esterification.

DETAILED DESCRIPTION OF INVENTION

The process of the instant invention is generally applicable to the formation of essentially monomeric esters using as starting materials any aliphatic alcohols and carboxylic acids which do not contain groups which otherwise interfere with the esterification reaction.

The process of the instant invention may be used to form mono esters by reacting an aliphatic alcohol containing a single hydroxyl group with a monocarboxylic acid. Examples of the hydroxy materials which may be esterified according to the instant invention include $C_1$–$C_{18}$ aliphatic monohydroxy compounds. Examples of such materials include alcohols such as methanol, ethanol, isopropanol, butanol and the like. Also encompassed within the "aliphatic alcohol" definition as used herein are aliphatic alcohols wherein the hydroxyl group maintains its aliphatic character even though it is part of a molecule which is substituted with an aromatic group such as, for example, 1-hydroxy2-phenylethane, 1-hydroxy2-phenylpropane and the like.

Aliphatic polyols may also be employed in the instant invention. In general, the polyols of the instant invention contain from about 2 to about 10 hydroxyl groups per molecule and up to about 36 carbon atoms, preferably about 2 to about 5 hydroxyl groups and up to about 18 carbon atoms. The polyols should be liquid at a temperature below about 300° C. and should contain no other groups which interfere with the esterification reaction. Examples of such polyols include the glycols including ethylene glycol, propylene glycol, hexanediol and the like; the triols such as glycerine, trimethylolpropane, trimethylolethane; and the tetraols, such as pentaethritol. Useful polyols may also be formed by etherifying the above-mentioned polyols. Examples of these materials include the polyglycols such as diethylene and triethylene glycols and the polypentaethritols such as di and tri pentaerythritol.

The carboxylic acids which are useful herein may be aliphatic or aromatic in character and may be represented by the general formula:

$$X(COOH)_n$$

wherein X is aliphatic or aromatic and n is 1 to 4. Thus, the carboxylic acid groups may be attached to the same or different carbon atoms and, in fact, to the same or different rings system. Examples of the monocarboxylic acids which are useful include acetic acid, propionic acid, butyric acid and the like. Also included are fatty acids having from about 12 to about 36 carbon atoms including materials such as linseed oil fatty acid, palmitic acid, stearic acid, oleic acid, linoleic acid, lauric acid, myristic acid, and linolenic acid. Of particular importance are the unsaturated monocarboxylic acids such as acrylic acid, methacrylic acid, ethacrylic acid and the like. Dicarboxylic acids are also contemplated within the scope of the instant invention. Examples of such dicarboxylic acids include the following acids as well as, where applicable, their corresponding anhydrides: maleic acid, fumaric acid, dimer acids of $C_{18}$–$C_{36}$ fatty acids, adipic acid, azelaic acid, sebacic acid and dicarboxylic acids such as phthalic acid, isophthalic acid and terephthalic acid. Also included are poly basic acids such as trimellitic anhydride and pyromellitic dianhydride.

In carrying out the esterification reaction specified above, an esterification catalyst may be employed although it is not necessary. In fact, one of the benefits of this invention resides in the fact that even with uncatalyzed systems, extremely rapid esterification can occur. The esterification catalyst, if used, should be added in the range of about 0.1–10 percent, preferably about 1–5 percent, based on the total weight of the reactants. Suitable esterification catalysts include paratoluene sulfonic acid (PTSA), methane sulfonic acid, dibutyl tin oxide, titanate esters and the like.

The esterification catalyst may be removed from the reaction medium by means of a cation exchange resin. This resin may be added directly to the reaction mixture and then filtered off, or the finished product may be passed through a cation exchange resin of the tertiary amine type. In the alternative, the insoluble salt of the reaction catalyst is formed such as by adding ammonia to a PTSA catalyst system. The reaction mixture is then filtered to remove the salted catalyst. In some cases, the esterification catalyst can be retained in the product when its presence will not have an adverse impact on the properties of the final product.

When the esterification process is carried out employing a polymerizable reactant, about 0.01-3.0 percent by weight, based on the total reaction mixture weight of a polymerization inhibitor is added to reduce the formation of polymer during esterification. Examples of such materials include the quinones, such as hydroquinone and its monomethyl ether, the various phenols, p-tert-butylcatechol, p-methoxyphenol, 2,4-dichloro-6-nitrophenol, n-propyl gallate, di-tert-butyl-p-cresol, 2,2'-methylenebis(4-methyl6-tertbutylphenol), 1-amino7-naphthol, p-benzoquinone, 2,6-dichloro-p-benzoquinone, 2-amino-1,4-napthoquinone, 3-aminoanthraquinone, diphenylamine, p-nitrosodimethylaniline, α and β-naphthylamine, nitrobenzene, phenothiazine, hexamethylphosphoramide, n-dodecyl mercaptan, benzenethiol, 2,2-diphenyl1-picrylhydrazyl (phenyl hydrazine), divinylacetylene, and various antimony and copper salts. Most preferred among the inhibitors are paramethoxyphenol, phenothiazine and nitrobenzene.

In order to activate the polymerization inhibitor, it is necessary to employ an oxygen containing sparge, such as an air sparge, particularly during the early stages of the esterification reaction.

The instant invention achieves significant reductions in esterification processing times for virtually any esterification reaction which is carried out. Reductions can range from as little as 20% in reaction time to as high as 400 to 500% or more. There are two basic alternative means of carrying out the process of the instant invention. One involves the addition, preferably at elevated temperatures, of the carboxylic acid to the hydroxyl reactant which has previously been charged into the reactor and heated to below its boiling point. The other alternative process involves the addition, preferably at elevated temperatures, of the hydroxyl reactant to the preheated carboxylic acid in the reactor.

In carrying out the process of the instant invention, regardless of whether the carboxylic acid or the hydroxyl material is initially charged into the reactor, it is essential that the contents of the reactor be heated to from about 100° C. to about the boiling point of the lowest boiling reactant. If the reaction temperature which is chosen exceeds the boiling point of the lowest boiling esterification reactant, the reactant will reflux out of the reactor. If a temperature of less than about 100° C. is chosen, the reaction speed is substantially reduced. Preferably the temperature is from about 110° C. to about 10° below the boiling point of the lowest boiling reactant. According to the process of this invention the material which is added to the reactor may also be heated up to the boiling point of the lowest boiling reactant although this step is not required.

The material which is added to the reactor is added over a period of time which is at least equal to the time necessary to remove, at reaction temperature, at least about 65 percent, preferably about 75 percent of the water of reaction from the reactor. Normally the minimum period of time will range from about 45 minutes to about one hour and 20 minutes. The maximum amount of time over which the material is added to the reactor depends upon the desired speed of the reaction. As the speed at which the material is added to the reactor is slowed, overall processing time will also be slowed. In general, the material should be added over to the reactor the fastest possible time consistent with the above standards.

The esterification reaction in the reactor is preferably carried out in the presence of a reflux solvent in order to facilitate the removal of water. The reflux solvent which is chosen should have a boiling point sufficient to form an azeotrope with water at above about 100° C. Examples of such solvents include xylene, toluene and other aromatic and aliphatic hydrocarbons having similar boiling points.

The reactor which is utilized to carry out the reaction is a conventional esterification reactor equipped with an addition reservoir to allow addition of the reactant over an extended period of time. The addition reservoir should be provided with a heating means to allow addition of the reactant at the desired temperature. The reactor should also be provided with a mechanical agitator, thermometer, sampling tube and water removal condensor.

In one alternative process of the instant invention, after the reactants have been added to the reactor, they are heated under reflux conditions for up to about two hours. By providing for a reflux holding period, it is possible to insure that the condensate from the reactor fully separates into two phases—one a water phase and the second a solvent phase with the solvent phase being returned to the reactor and the water being removed. If the reflux holding period is not employed, in some cases an undesirably large amount of reactant may be removed from the reactor. When employing this alternative process, it is necessary for the reactor to be equipped with a means to switch from a reflux condensor in which the refluxing materials are condensed and returned to the reactor to a conventional water take-off condensor wherein water is removed from the reactor during processing.

In order to insure that rapid esterification occurs, the reactants are maintained at the highest possible temperature consistent with efficient water removal. The temperature in the reactor is increased as rapidly as possible to allow sufficient removal of the water and, when the esterification is completed as measured the acid value of the reactants being less than about 10, the reaction is deemed complete.

The product prepared according to the method of the instant invention may then be processed as any conventional ester by carrying out various purification steps including filtering, washing, straining, distillation and the like. These esters find particular utility as lubricants and as dielectric fluids.

In the following examples all part and percentages are by weight unless otherwise indicated.

EXAMPLES

Example 1

Into a reactor equipped with a mechanical agitator, heating device, thermometer, sampling device and water take-off condensor were added 1.0 mols of trimethylolpropane (TMP) and 3.15 mols of pelargonic acid. The reactants were heated until the theoretical amount of water had been removed. Processing temperatures ranged from 140° C. initially to 260° C. at the end of the reaction. The final product exhibited an acid value of 11.3. Total reaction time was 16 hours.

Example 2

Example 1 was repeated except that the molar ratio of the pelargonic acid to trimethylolpropane was decreased to 2.9 to 1. The process of Example 1 was employed except that the pelargonic acid and the trimethylol propane were preheated to 219° C. to 222° C. and held at this temperature for about a one hour period during which time the pelargonic acid was added to the heated trimethylol propane in the reactor at a uniform rate. The reaction temperature during the acid addition period ranged from 219° C. to 260° C. The resulting product required five hours to process to an acid value of 7.4.

Example 3

Example 2 was repeated except that the trimethylolpropane was added over about a 40 minute period while it was maintained at a temperature of 216° C. to 220° C. During the addition the pelargonic acid present in the reactor and the contents of the reactor were also maintained at about 220° C. The reaction processing time was five hours and the product had an acid number of 6.6. During the reaction, processing temperatures ranged from 216° C. to 260° C.

Example 4

Utilizing essentially the same reactor as described in Example 1, 3.1 moles of pelargonic acid were added to the reactor along with 1 mole of trimethylolpropane. Also added to the reactor was 0.05 percent by weight of dibutyl tin oxide. The contents of the reactor were heated to reaction temperature and the reaction temperature was allowed to increase until the theoretical water of reaction had been removed. The processing time was 4.5 hours and the resulting product exhibited an acid number of 5.7.

Example 5

Example 4 was repeated except that the reaction ratio was 1 mol of trimethylolpropane to 3.0 mols of pelargonic acid. In addition instead of charging all reactants to the reactor at the beginning of the reaction, the pelargonic was preheated to a temperature of 236° C. to 241° C. and added to the reactor over a two hour period. During the addition the contents of the reactor were maintained at the same temperature. The processing time for the reaction was 4 hours and the resulting product exhibited an acid value of 3.9.

Example 6

Example 5 was repeated except that the trimethylolpropane was hot fed into the reactor rather than the pelargonic acid. In addition, the trimethylolpropane was added over a 52 minute period with the temperature of the trimethylolpropane being maintained between 215° C. and 227° C. Three hours were required to complete the reaction and the resulting product exhibited an acid value of 1.2.

Example 7

Into a reactor equipped with a mechanical agitator sampling device, thermometer, heating means and water take off condensor were added 1 mole of trimethylolpropane and 3.3 moles of acrylic acid. Also added to the reactor was 3.5 percent by weight of toluene, 0.5 percent by weight of methane sulfonic acid and 0.1 percent by weight of hydroquinone. An air sparge was started into the reactor. The contents of the reactor were heated over a 10 hour period to 135° C. A product resulted having an ester rank of 2.8.

Example 8

Example 7 was repeated except that the trimethylolpropane was preheated to about 135° to 150° C. and added to the reactor over a 110 minute period to the acrylic acid which had been heated to 120° C. During the first 50 minutes of addition no distillate was recovered from the reactor but was returned to the reactor via a reflux comdensor. At this point a Dean Stark trap was placed in the system and the water distillate was removed. The entire reaction period was about 5 hours. The resulting product exhibited an acid number of 0.11, a weight percent of free acrylic acid of 0.013 and a viscosity of 135 cps.

The figure attached shows a comparison of the distillate collected versus processing time for Example 7 and Example 8. Two conclusions are readily apparent. The first is that the processing time, i.e., the time which is required to proceed to the same point in the reaction sequence is much quicker for Example 8 than it is for Example 7 after an initial induction phase. The second conclusion which can be drawn from the figure is that the reaction kinetics for the esterification in question have been significantly altered as between Example 7 and Example 8.

Example 9

Into a reactor equipped as in Example 8 were added 780.1 parts of methacrylic acid, 35.0 parts of toluene, 5.0 parts of methane sulfonic acid and 1.0 parts of phenothiazine. An air sparge was begun. The contents of the reactor were heated to about 118° C. and the addition of 368.3 parts trimethylolpropane maintained at 128° C. was begun. The TMP was added to the reactor over a 100 minute period and the reaction was held at reaction temperature for about 5 hours producing a finished polyacrylate ester.

Example 10

Into a reactor equipped as in Example 8 were added 406.9 parts of trimethylolpropane, 35 parts of toluene, 0.5 parts of hydroquinone and 1.0 part of methane sulfonic acid. The contents of the reactor were heated to 122° C., an air sparge was begun and the addition of 721.5 parts of acrylic mixed with 4.0 parts of methane sulfonic acid and 0.5 parts of hydroquinone was carried out over a 4.5 hour period. The reaction was continued at 122° to 134° C. for two more hours to produce a completed reaction product.

What is claimed is:

1. A process for the batch preparation of a mono carboxylic acid ester by reacting a mono carboxylic acid with an aliphatic hydroxyl containing compound, both of which have a boiling point of above about 100° C., which comprises:
   adding the mono carboxylic acid to a reactor, heating the contents of the reactor to a temperature of from about 100° C. to about the boiling point of the lowest boiling esterification reactant, adding the aliphatic hydroxyl compound to the reactor over at least about the time necessary to remove at least about 65 percent of the total water of reaction, and heating the reaction mixture until the reaction is complete.

2. A process for the batch preparation of a mono acrylate ester by reacting a mono carboxylic acid with an aliphatic hydroxyl containing compound, both of which have boiling points above about 100° C., which comprises:

adding the aliphatic hydroxyl containing compound to a reactor, heating the contents of the reactor to a temperature of from about 100° C. to about the boiling point of the lowest boiling esterification reactant, adding the mono carboxylic acid to the reactor over at least about the time necessary to remove at least about 65 percent of the total water of reaction, and heating the reaction mixture until the reaction is complete.

3. The process of claims 1 or 2 wherein the esterification is carried out in the presence of an esterification catalyst.

4. The process of claims 1 or 2 wherein the material added to the reactor over a period of time is heated.

5. The process of claim 4 wherein the material added to the reactor over a period of time is heated to the temperature of no greater than the boiling point of the lowest boiling esterification reactant.

6. The process of claim 2 wherein the esterification catalyst is selected from paratoluene and methane sulfonic acids.

7. The process of claim 2 wherein the mono carboxylic acid is added to the reactor over at least the period necessary to remove at least about 75 percent of the water of reaction.

8. The process of claim 1 wherein the aliphatic hydroxy compound is added to the reactor over at least the period necessary to remove at least about 75 percent of the water of reaction.

9. The process of claims 1 or 2 wherein, after all reactants are added to the reactor, the contents of the reactor are heated without water removal for up to about 120 minutes.

10. The process of claims 1 or 2 wherein the aliphatic hydroxyl compound is a polyol having from 2 to 10 hydroxyl groups and containing up to about 36 carbon atoms per molecule.

11. The process of claim 10 wherein the polyol is selected from glycerine, trimethylolpropane, trimethylolethane and mono and polypentaerythritols and glycols.

12. A process for the batch preparation of an ester of a mono carboxylic acid by reacting said mono carboxylic acid with an aliphatic polyhydroxy polyol having 2 to 10 hydroxyl groups and containing up to 36 carbon atoms per molecule, wherein both the mono carboxylic acid and the aliphatic polyhydroxy polyol have a boiling point above about 100° C., in the presence of an esterification catalyst which comprises:

adding the mono carboxylic acid to a reactor, heating the acid to a temperature of from about 100° C. to about the boiling point of the lowest boiling esterification reactant, adding the aliphatic polyol to the reactor over at least about the time necessary to remove at least about 65 percent of the total water of reaction and heating the reaction mixture until the reaction is complete.

13. A process for the batch preparation of a mono carboxylic acid ester by reacting a mono carboxylic acid with an aliphatic polyhydroxyl polyol having from 2 to 10 hydroxyl groups and containing up to about 36 carbon atoms per molecule, wherein both the mono carboxylic acid and the aliphatic polyhydroxy polyol have a boiling point above about 100° C., in the presence of an esterification catalyst which comprises:

adding the polyol to a reactor, heating the polyol to a temperature of from about 100° to about the boiling point of the lowest boiling esterification reactant, adding the mono carboxylic acid to the reactor over at least the time necessary to remove about 65 percent of the total water of reaction and heating the reaction mixture until the reaction is complete.

14. The process of claims 1, 2, 12 or 13 wherein a reflux solvent is employed.

15. The process of claims 1, 2, 12, and 13 wherein a reflux solvent having a boiling point sufficient to form an azeotrope with water at above about 100° C. is employed.

16. The process of claim 14 wherein the reflux solvent is xylene or toluene.

17. The process of claim 15 wherein the azeotrope solvent is xylene or toluene.

18. The process of claims 1, 2, 12 and 13 wherein an oxygen containing sparge is employed.

* * * * *